(12) United States Patent
Perry

(10) Patent No.: US 11,654,048 B2
(45) Date of Patent: May 23, 2023

(54) DSAEK CORNEAL GRAFT ASSEMBLIES FOR OPTIMIZED SURGICAL OPERATIONS

(71) Applicant: The North Carolina Eye Bank Inc, Winston Salem, NC (US)

(72) Inventor: Isaac Perry, Winston Salem, NC (US)

(73) Assignee: MIRACLES IN SIGHT, Winston Salem, NC (US)

( * ) Notice: Subject to any disclaimer, the term of this patent is extended or adjusted under 35 U.S.C. 154(b) by 0 days.

(21) Appl. No.: 17/652,089

(22) Filed: Feb. 22, 2022

(65) Prior Publication Data

US 2022/0175509 A1 Jun. 9, 2022

Related U.S. Application Data

(60) Continuation-in-part of application No. 16/989,057, filed on Aug. 10, 2020, which is a division of application No. 16/392,259, filed on Apr. 23, 2019, now Pat. No. 10,806,558.

(51) Int. Cl.
| | |
|---|---|
| *A61F 9/007* | (2006.01) |
| *A61F 2/00* | (2006.01) |
| *A61F 2/14* | (2006.01) |
| *A01N 1/02* | (2006.01) |

(52) U.S. Cl.
CPC ............ *A61F 9/007* (2013.01); *A01N 1/0273* (2013.01); *A61F 2/0095* (2013.01); *A61F 2/142* (2013.01); *A61F 2/148* (2013.01)

(58) Field of Classification Search
CPC ........ A61F 2/0095; A61F 2/142; A61F 2/148; A61F 9/007; A01N 1/0273
See application file for complete search history.

(56) References Cited

U.S. PATENT DOCUMENTS

| | | | |
|---|---|---|---|
| 8,029,515 B2 | 10/2011 | Shiuey | |
| 8,470,029 B2 * | 6/2013 | Walter | .............. A61F 2/142 |
| | | | 623/6.12 |
| 9,999,497 B2 | 6/2018 | Shiuey | |
| 10,041,865 B2 | 8/2018 | Tran | |

(Continued)

FOREIGN PATENT DOCUMENTS

| | | |
|---|---|---|
| CH | 708083 A1 | 11/2014 |
| GB | 2521360 A | 6/2015 |

(Continued)

OTHER PUBLICATIONS

Iselin, K.C., Greenan, E., Hynes, C. et al. Changing trends in corneal transplantation: a national review of current practices in the Republic of Ireland. Ir J Med Sci. 2021; 190: 825-834.

(Continued)

*Primary Examiner* — William H Matthews
(74) *Attorney, Agent, or Firm* — ePatentManager.com; Guerry L. Grune

(57) ABSTRACT

Assemblies for storing, handling, transporting, viewing, evaluating, and/or shipping corneal tissue are provided. The assembly includes a corneal tissue carrier, optimized for DSAEK and UT-DSAEK corneal grafts, within a transport vial, the transport vial removably coupled to a stabilization base, wherein the ease of access to the graft carrier allows administering the corneal tissue sample to a patient in rapid succession so that more surgeries can be performed by a single surgeon in a single day.

26 Claims, 4 Drawing Sheets

(56) References Cited

U.S. PATENT DOCUMENTS

| | | |
|---|---|---|
| 2010/0057093 A1 | 3/2010 | Ide et al. |
| 2013/0085567 A1 | 4/2013 | Tan et al. |
| 2013/0274875 A1 | 10/2013 | Ide et al. |
| 2013/0317605 A1 | 11/2013 | Ide et al. |
| 2017/0095325 A1 | 4/2017 | Plambeck et al. |
| 2017/0340428 A1 | 11/2017 | Szurmann et al. |
| 2019/0038400 A1 | 2/2019 | Samudre |
| 2020/0206029 A1* | 7/2020 | Abdullayev ............ A61F 2/142 |

FOREIGN PATENT DOCUMENTS

| | | |
|---|---|---|
| WO | 2008096821 A1 | 8/2008 |
| WO | 2012065602 A2 | 5/2012 |
| WO | 2017201213 A1 | 11/2017 |
| WO | 2018208729 A1 | 11/2018 |

OTHER PUBLICATIONS

Stuart, AJ, Romano, V., Virgili, G., Shortt, A.,Descemet's membrane endothelial keratoplasty (DMEK) versus Descemet's stripping automated endothelial keratoplasty (DSAEK) for corneal endothelial failure (Review). Cochrane Database of Systematic Reviews 2018, Issue 6. Art. No. CD012097. DOI: 10.1002/14651858. CD012097.pub2.

Dekaris, I. Ultra-thin Descemet Stripping Automated Endothelial Keratoplasty (UT-DSAEK)—why I prefer this technique?. Svjetlost Eye Clinic. 5th International Conference on Clinical & Experimental Ophthalmology, Valencia, Spain, 2015.

Woodward, M.A., Titus, M., Mavin, K., Shtein, R.M. Corneal Donor Tissue Preparation for Endothelial Keratoplasty. J. Vis. Exp. (64), e3847, doi:10.3791/3847 (2012).

Marques, et al. DMEK versus DSAEK for Fuchs' endothelial dystrophy: A meta-analysis. European Journal of Opthalmology 2019, vol. 29(1) 15-22.

Gangwani, et al., A Prospective Study Comparing EndoGlide and Busin Glide Insertion Techniques in Descemet Stripping Endothelial Keratoplasty. American Journal of Ophthalmology. 2011.

Stuart, Annie. Performing DSAEK: A Step-by-Step Guide. Clinical Update: Cornea. Eyenet. p. 25-27. Jan. 2014.

Pre-Loaded DSAEK Tissue. Eversight Services. Surgeon Sheets. Revised Jan. 22, 2018.

Palioura, et al. Outcomes of Descemet Stripping Endothelial Keratoplasty Using Eye Bank-Prepared Preloaded Grafts. Cornea. vol. 36, No. 1, Jan. 2017.

* cited by examiner

DSAEK CORNEAL GRAFT ASSEMBLIES FOR OPTIMIZED SURGICAL OPERATIONS

PRIORITY

This application is a continuation-in-part of Ser. No. 16/989,057 filed Aug. 10, 2020, which is a divisional of and claims priority under US 35 USC 120 from U.S. application Ser. No. 16/392,259, entitled "Corneal Graft Assemblies for Improved Surgical Operations", filed Apr. 23, 2019, and granted as U.S. Pat. No. 10,806,558 on Oct. 20, 2020.

The above referenced applications are hereby incorporated by reference in their entirety.

DESCRIPTION

Technical Field

The present disclosure relates generally to corneal tissue graft assemblies. More specifically, the present disclosure relates to human or animal tissue sample devices that allow for storage, handling, transportation, visualizing and/or evaluation of the tissue prior to and during surgical operations. Even more specifically, the present disclosure provides for use of the devices with corneal tissue. The present disclosure also relates to surgical method(s) optimization using such devices for administering corneal tissue grafts to subjects in need thereof.

Background

Over the past century, advances in instrumentation and eye banking have allowed for the evolution and refinement of the surgical technique of keratoplasty. What began as full thickness tissue transplantation, or Penetrating Keratoplasty (PK), has expansively evolved into partial thickness or lamellar grafts, including the various forms of Endothelial Keratoplasty (EK) like Descemet Membrane Endothelial Keratoplasty (DMEK) and Descemet Stripping Automated Endothelial Keratoplasty (DSAEK) and Ultrathin DSAEK (UT-DSAEK) (see Iselin, K. C., Greenan, E., Hynes, C. et al. Changing trends in corneal transplantation: a national review of current practices in the Republic of Ireland. *Ir J Med Sci*. 2021; 190: 825-834).

DMEK is a partial thickness corneal transplantation procedure that enables a one-for-one replacement of a diseased Descemet's membrane and endothelium complex (see Melles G R, et al. *Cornea*. 2002; 21:415-418; Melles G R, et al. *Cornea*. 2006; 25:987-990; and Price M O, et al. *Int Ophthalmol Clin*. 2010; 50:137-147). DMEK may provide improved post-operative visual outcomes, faster recovery times, and reduced rates of rejection compared to other endothelial keratoplasty procedures such as DSAEK and PK (see Hamzaoglu E C, et al. *Ophthalmology*. 2015; Anshu A, et al. *Ophthalmology*. 2012; 119:536-540; Guerra F P, et al. *Ophthalmology*. 2011; 118:2368-2373; Tourtas T, et al. *Am J Ophthalmol*. 2012; 153:1082-1090 e1082; Guerra F P, et al. *Cornea*. 2011; 30:1382-1386; and Ham L, et al. *Arch Ophthalmol*. 2009; 127:252-255). While DMEK is a widely used procedure, DSAEK and PK remain the most widely performed corneal transplant procedures worldwide, (see Eye Bank Association of America. 2018 *Eye Banking of America Statistical Report*. Washington D.C.: Eye Bank Association of America; 2019). Background features of DMEK and DSAEK grafts and respective surgical techniques are provided in Table 1.

TABLE 1

| DMEK vs. DSAEK | |
| --- | --- |
| DMEK | DSAEK |
| ~15 µm graft comprising endothelial cells and Descemet's Membrane | ~70 µm graft comprising endothelial cells and Descemet's Membrane, and stromal collagen |
| Fragile graft | "Tougher" graft |
| Touchless techniques utilizing fluid movement to influence graft motion | More mechanical techniques |
| Graft does not swell in media | Graft can sell in aqueous environment due to exposed, sponge-like collagen |

As for the specific differences, may be more technically challenging to learn and perform the surgical technique compared with an ultrathin DSAEK. DMEK donor tissue is also more difficult to prepare as it does not contain any stromal tissue and is therefore thinner and more fragile than a DSAEK graft. The re-bubble rate for DMEK varies widely according to the literature and is significantly higher than that of DSAEK and/or UT-DSAEK. DMEK is not easily accomplished for eyes that are phakic or have aphakia, aniridia, significant iris trauma, an anterior chamber IOL, a trabeculectomy, or a tube shunt. DSAEK or UT-DSAEK is often a preferred option in such eyes, depending on surgeon diagnosis and/or graft preference. (see Saha, S. Ultrathin DSAEK vs. DMEK. Peer Review. *Millenial Eye*. September/October 2015. https://millennialeye.com/articles/2015-sept-oct/ultrathin-dsaek-vs-dmek/).

With preloaded corneal graft tissue gaining popularity among surgeons, eye banks have developed internal processing programs to assist surgeons in preparing DSAEK, UT-DSAEK, and DMEK grafts (see Eye Bank Association of America. 2018 *Eye Banking of America Statistical Report*. Washington D.C.: Eye Bank Association of America; 2019; Holiman J, et al. In: Mohit Parekh.; Stefano Ferrari D P, ed. *Eye Banking: Nova Biomedical;* 2015:123-139; Deng S X, et al. *Am J Ophthalmol*. 2015; 159:590-596; and Terry M A, et al. *Cornea*. 2015; 34:845-852). Eye bank prepared pre-stripped, pre-peeled, and/or pre-loaded tissues can help reduce both time in the operating room (OR) and potential complications that may arise if tissue preparation fails during surgery. Pre-stripped, pre-peeled, and/or pre-loaded tissues can also provide an additional level of quality assurance as eye banks can perform post-processing evaluation of grafts using tissue evaluation instruments and methods, such as, specular microscopy, slit-lamp biomicroscopy, light microscopy, and/or optical coherence tomography, which are not typically performed in the OR.

US Patent Application No. 2017/0340428 provides a corneal tissue storage and transport kit, where a graft carrier is removably secured to a transport bracket that may be positioned in a 20 mL or 50 mL flask. The glass graft carrier, capped on each end, is removed from the transport bracket using a counter-resistive prying force. The graft carrier has one end tapered for insertion into the surgical site, while the opening on the opposing end is larger and non-tapered allowing for the graft carrier to slip onto a syringe. The device comprises a container, which can be filled with a medium, preferably a nutrient medium, and a receiving device, which can be arranged in the container for the graft or implant. The graft or implant is arranged in a separate receiving device in the container. As a result, the graft or implant is securely handled by means of the receiving device and, at the same time, the graft or implant secured in the receiving device is protected in the container.

U.S. Pat. No. 10,041,865 provides an assembly for storing and evaluating corneal tissue, the assembly having a viewing chamber with a body and a lid; and a corneal tissue carrier removably coupled to an inner portion of the body of the viewing chamber. A corneal tissue sample assembly is also described as having an inner cavity with an opening on each end to which two removable plugs are provided to close or seal the corneal tissue sample within the cavity.

U.S. Pat. No. 10,806,558 provides an assembly kit for DMEK corneal tissue graft transport and sterile retrieval during surgical procedures. Similarities to the present disclosure include transport/delivery devices for EK (Endothelial Keratoplasty procedures), use of the same vial, use of luer lock adaptors, luer lock cap, and smaller vented tips (of different sizes), require poly-cone lid, utilize 3-D printed stability base, benefit from gentle compression that is released when the lid is removed, no counter-resistive force is required for removal of the assembly, similar preparation steps for the surgeon in the OR, and both save a great deal of time and stress for the operating surgeon. While there are similarities, there are also key differences. The current configuration of this graft carrier is for DMEK graft preparation, transport, and retrieval and therefore does not allow for the proper processing, transport, and retrieval of prepared DSAEK and UT-DSAEK corneal grafts. Therefore, the present disclosure includes the objective of providing a device and a set that is an assembly of sterile components which allow for a secure support and/or secure transport, as well as providing a secure and simple graft or implant as the graft or implant is introduced into a human or an animal body.

Benefits of the present disclosure include significant volume reduction of storage medium, locking connection(s) between the tissue transport assembly and a syringe, ease of access to the tissue transport assembly, elongated tissue transport device, and a stabilizing device. Such benefits allow for a simplified OR (operating procedure) preparation, and notable time savings, which can lead to an increase in the number of surgeries performed by a capable surgeon in a given day.

For the present disclosure, the surgeon does not need to trephine/cut out the graft, which saves time, is safer, and allows for an improved quality check in eye-bank environment. The surgeon may choose not to load the graft into a separate insertion device, saving time, equipment, and costs.

The thin-walled glass tube maximizes the graft carrier tube's inner diameter, preventing graft compression and folding. This contributes to minimal cell loss compared to other devices and insertion techniques.

Known orientation of the graft in the carrier device allows the surgeon to easily identify which side is in the upward direction and eject the graft accordingly, so there is minimal manipulation required once inserted in the eye of the patient. In most cases the graft is tissue which in this case is defined as an intricate structure or network made from a number of connected items.

Further safety advantages are offered in the present disclosure. Breakage of glass graft carriers may occur when the graft carrier is directly engaged by forceps or hemostats and/or pried loose from prongs used to secure the carrier during transport, such as in other commercially available graft devices/kits provided and described above. Elimination of breakage is successful through forcep engagement of the graft carrier at the cap of the luer-locking device, preventing the need for a metal to glass interaction. Breakage, slippage, and/or spillage is also eliminated as there is no coupling of the graft carrier to the vial or any form of transport bracket, thereby eliminating the counter-resistive force required to remove the graft carrier from the coupling. Minor compression forces secure the present disclosure in a safe manner such that the force is relieved upon opening the vial lid.

Additionally, the reduction in surgical time translates to hospital or surgical center cost savings, while performing more reliable procedures per day. Quicker surgery may translate to greater efficiency with respect to patient anesthesia dosing. The use of the present assemblies and associated operating procedures also provide for increased revenue for the hospital and/or clinic where the procedures are performed.

Preservation of the graft near a sterile field is achieved through a stabilizing base that provides support to prevent spillage while maintaining a proper preferred position of the graft carrier. The elongation of the graft carrier assembly reduces the likelihood of aspiration of the graft into a syringe before and/or during the surgical procedure.

SUMMARY

Assemblies for storing, handling, transporting, viewing, evaluating, and/or shipping corneal tissue are provided. The assembly includes a corneal tissue carrier within a vial, the transport vial removably coupled to a stabilization base, wherein the ease of access to the graft carrier allows administering the corneal tissue sample to a patient in rapid succession so that more surgeries can be performed by a single surgeon in a single day.

More specifically, the present disclosure describes a vial with a vial lid that includes a poly-cone insert so that the vial lid and a vented cap on the DSAEK fitted assembly compressively secures the DSAEK fitted assembly graft carrier within the vial, a support base that provides support so that the vial is able to stand upright and remain motionless, a collarless luer locking cap, a luer locking connector that includes both a female luer locking end and a barbed male end, wherein the female luer locking end connects with the luer locking cap and wherein the barbed male end is slideably coupled to flexible, nonbeveled tubing, that completes a connection between additional beveled tubing and two glass sections such that one glass section is a corneal tissue graft carrier holding portion that is a non-tapered straight glass tube with a largest opening at a beveled end of the straight glass tube and a second glass section with a spacer portion that provides a rigid connection between beveled flexible tubing and nonbeveled flexible tubing so that a double-flanged glass tube connects to the straight glass tube and luer lock connector and such that the DSAEK assembly provides a graft contained within the complete DSAEK fitted assembly.

Herein the beveled flexible tubing is connected to a bottom flange of the double-flanged glass tubing and is further connected to a nonbeveled flexible tubing and wherein the inlet luer locking mechanism and complete fitted assembly reduces surgical operating room (OR) time by at least two minutes and wherein the graft is tissue.

In addition, the corneal tissue carrier provides an acceptable lack of counter-resistive forces so that retrieval of the graft from the vial is easily extracted by one or more medical professionals, thus reducing retrieval time, potential for breakage of the corneal tissue carrier, and reduces and/or eliminates risk of tipping the completed assembly.

In this embodiment, a folded DSAEK graft is accommodated that is in a thickness range of less than 80 µm thick and wherein the folded DSAEK graft includes a traditional layer of endothelial cells on an inside portion of the DSAEK graft.

In this case, a female luer locking end connects with a syringe after the collarless luer locking cap has been removed so that the completed fitted assembly provides an ability to directly eject tissue into a patient's eye, specifically an anterior chamber and/or cornea by a surgeon, and wherein the tissue is held within the tissue carrier with a flexible cap with orifices arranged circumferentially and perpendicular to an opening of the tissue carrier that is removably coupled with a beveled end of the tissue carrier.

Also, the tissue carrier is a corneal tissue carrier that carries corneal tissue and wherein the corneal tissue carrier is a modified ophthalmic tube that includes a modified Jones tube or other modified tube-shaped device.

In another embodiment, the collarless luer locking cap includes a small indention that accepts a tip of at least one of a group consisting of forceps, microforceps, hemostat, and suitable sterile device that allows for ease of grasp of the tissue from the completed fitted assembly and ease of retrieval of the tissue from the vial and wherein the vial has a base that is either a circular or square-shaped, or the vial is cylindrical and includes at least one flat plane portion.

In yet another embodiment the tissue carrier is comprised of either transparent or translucent glass, thermoplastics, and/or silicone polymers, and is designed to hold a lamellar cornea graft, that may be a scrolled or folded corneal tissue graft, from either a primary cell donor or obtained via ex vivo cellular expansion methods that can be seen and inspected by a surgeon prior to and during an operation that utilizes the corneal tissue.

The tubing can be flexible and pliable tubing and the tubing comprises materials that are flexible, pliable or rigid materials selected from one or more of a group consisting of silicone, silicone rubber, thermoplastics, thermosets, metals, and ceramics.

The syringe is optionally included with the kit.

In another embodiment, the Descemet's Stripping Automated Endothelial Keratoplasty (DSAEK) fitted assembly is a corneal graft carrier for supporting and transporting a graft or implant or tissue wherein the fitted assembly further comprises a vial with a vial lid that includes a poly-cone insert so that the vial lid and a vented cap on the DSAEK fitted assembly compressively secures the DSAEK fitted assembly graft carrier within the vial, a support base that provides support so that the vial is able to stand upright and remain motionless, a collarless luer locking cap, a luer locking connector that includes both a female luer locking end and a barbed male end, wherein the female luer locking end connects with the luer locking cap and wherein the barbed male end is slideably coupled to flexible, nonbeveled tubing, that completes a connection between additional beveled tubing and two glass sections such that one glass section is a corneal tissue graft carrier holding portion that is a non-tapered straight glass tube with a largest opening at a beveled end of the straight glass tube and a second glass section with a spacer portion that provides a rigid connection between beveled flexible tubing and nonbeveled flexible tubing so that a double-flanged glass tube connects to the straight glass tube and luer lock connector and such that the DSAEK assembly provides a graft contained within the complete DSAEK fitted assembly.

In the present disclosure a method is provided for performing tissue repair or replacement surgery that includes utilizing a (DSAEK) fitted assembly within a vial filled with storage media fluid and a graft or implant for supporting and transporting the graft or implant such that when a graft or implant held within the assembly arrives for surgery, a surgeon inspects the graft or implant and the surgeon simply retrieves the fitted assembly that functions as a graft or implant carrier, removes a luer locking cap and attaches a syringe filled with a balanced salt solution (BSS) to a female luer locking connector wherein the fitted assembly includes flexible tubing and an inlet luer-locking mechanism allowing the surgeon quick and simple access to the graft or implant and rapid completion of surgery to replace or repair the tissue.

The tissue repair or replacement surgery is a lamellar keratoplasty surgery utilizing primary cells from a donor, or cells that are obtained via ex vivo methods, which in often includes endothelial keratoplasty, specifically, DSAEK or UT-DSAEK surgery.

An additional method of using a completed DSAEK fitted assembly for supporting and transporting a graft or implant that is a tissue, is presented where the DSAEK fitted assembly comprises; a vial with a vial lid that includes a poly-cone insert so that the vial lid and a vented cap on the DSAEK fitted assembly compressively secures the DSAEK fitted assembly graft carrier within the vial, a support base that provides support so that the vial is able to stand upright and remain motionless, a collarless luer locking cap, a luer locking connector that includes both a female luer locking end and a barbed male end, wherein the female luer locking end connects with the luer locking cap and wherein the barbed male end is slideably coupled to flexible, nonbeveled tubing, that completes a connection between additional beveled tubing and two glass sections such that one glass section is a corneal tissue graft carrier holding portion that is a non-tapered straight glass tube with a largest opening at a beveled end of the straight glass tube and a second glass section with a spacer portion that provides a rigid connection between beveled flexible tubing and nonbeveled flexible tubing so that a double-flanged glass tube connects to the straight glass tube and luer lock connector and such that the DSAEK assembly provides a graft contained within the complete DSAEK fitted assembly.

The tissue carrier is a corneal tissue carrier that carries corneal tissue and wherein the corneal tissue carrier is a modified Jones tube or other a modified tube-shaped device and the tissue carrier includes a flexible cap with orifices arranged circumferentially and perpendicular to an opening of said tissue carrier that is removably coupled with a beveled end of the tissue carrier.

In another embodiment, the collarless luer locking cap includes a small indention that accepts a tip of at least one of a group consisting of: forceps, microforceps, hemostat, and suitable sterile device that allows for ease of grasp of the tissue from the completed fitted assembly and ease of retrieval of the tissue from the vial.

In at least one embodiment, the tissue carrier is comprised of either transparent or translucent glass, thermoplastics, and/or silicone polymers, and is designed to hold a lamellar cornea graft, that includes possibly a scrolled or folded corneal tissue graft, from either a primary cell donor or obtained via ex vivo cellular expansion that can be observed and inspected by a surgeon prior to and during an operation that utilizes the corneal tissue.

As before the tubing can be flexible and pliable tubing and wherein the tubing comprises materials that are flexible, pliable or rigid materials selected from one or more of a group consisting of silicone, silicone rubber, thermoplastics, thermosets, metals, and ceramics.

BRIEF DESCRIPTION OF THE DRAWINGS

The embodiments disclosed herein will become more fully apparent from the following description and appended claims, taken in conjunction with the accompanying drawings. While various aspects of the embodiments are presented in drawings, the drawings depict only typical embodiments, which will be described with additional specificity and detail through use of the accompanying drawings in which:

DETAILED DESCRIPTION

Figure 1A:
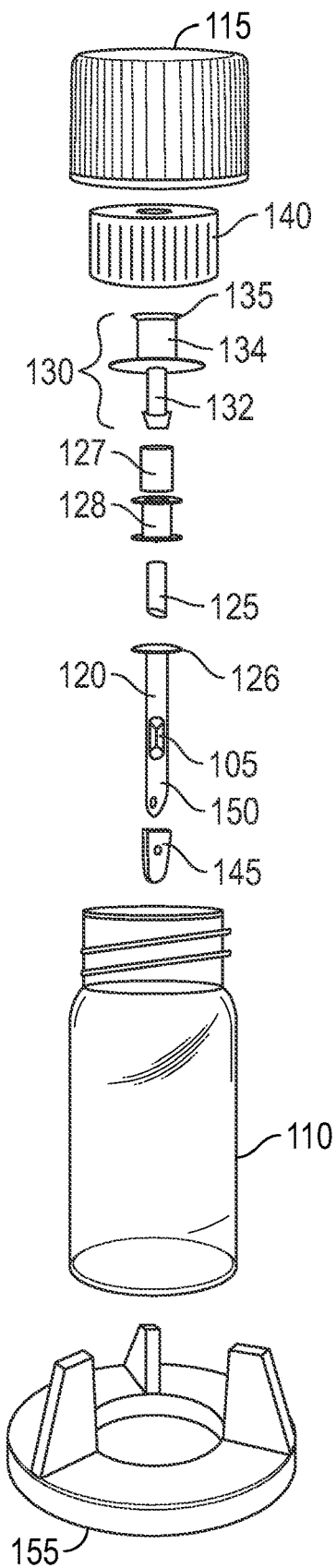
FIG. 1A is an exploded view of a corneal tissue sample assembly with corneal tissue carrier and stabilization attachment.

The various embodiments disclosed herein generally relate to assemblies for storing, handling, transporting, viewing, evaluating, and/or shipping corneal tissue. The assemblies include a vial, and a corneal tissue (graft) carrier. The assemblies may also include a corneal tissue (graft) sample, wherein the corneal tissue sample is disposed within the corneal tissue carrier.

Various features of the corneal tissue sample assemblies disclosed herein may be grouped together in a single embodiment, figure, or description thereof for the purpose of streamlining the disclosure. Many of these features may be used alone and/or in combination with one another in the various embodiments.

Embodiments may be understood by reference to the drawings, wherein like parts are designated by like numerals throughout. It will be readily understood that the components of the present disclosure, as generally described and illustrated in the drawings herein, could be arranged and designed in a wide variety of different configurations. Thus, the following more detailed description of the embodiments of the assembly is not intended to limit the scope of the disclosure but is merely representative of possible embodiments of the disclosure. In some cases, well-known structures, materials, or operations are not shown or described in detail. While the various aspects of the embodiments are presented in drawings, the drawings are not necessarily drawn to scale unless specifically indicated.

The phrases "connected to," "coupled to," and "in communication with" refer to any form of interaction between two or more entities, including but not limited to mechanical, electrical, magnetic, electromagnetic, fluid, and thermal interaction. Two components may be coupled to each other even though they are not in direct contact with each other. For example, two components may be coupled to each other through an intermediate component. The phrase "fluid communication" is used in its ordinary sense and is broad enough to refer to arrangements in which a fluid (e.g., a gas or a liquid) can flow from one element to another element when the elements are in fluid communication with each other.

FIG. 1A is an exploded view of the assembly [100] for storing, handling, transporting, viewing, evaluating, and/or shipping corneal tissue [105] (also referred to herein as a graft).

Figure 4:
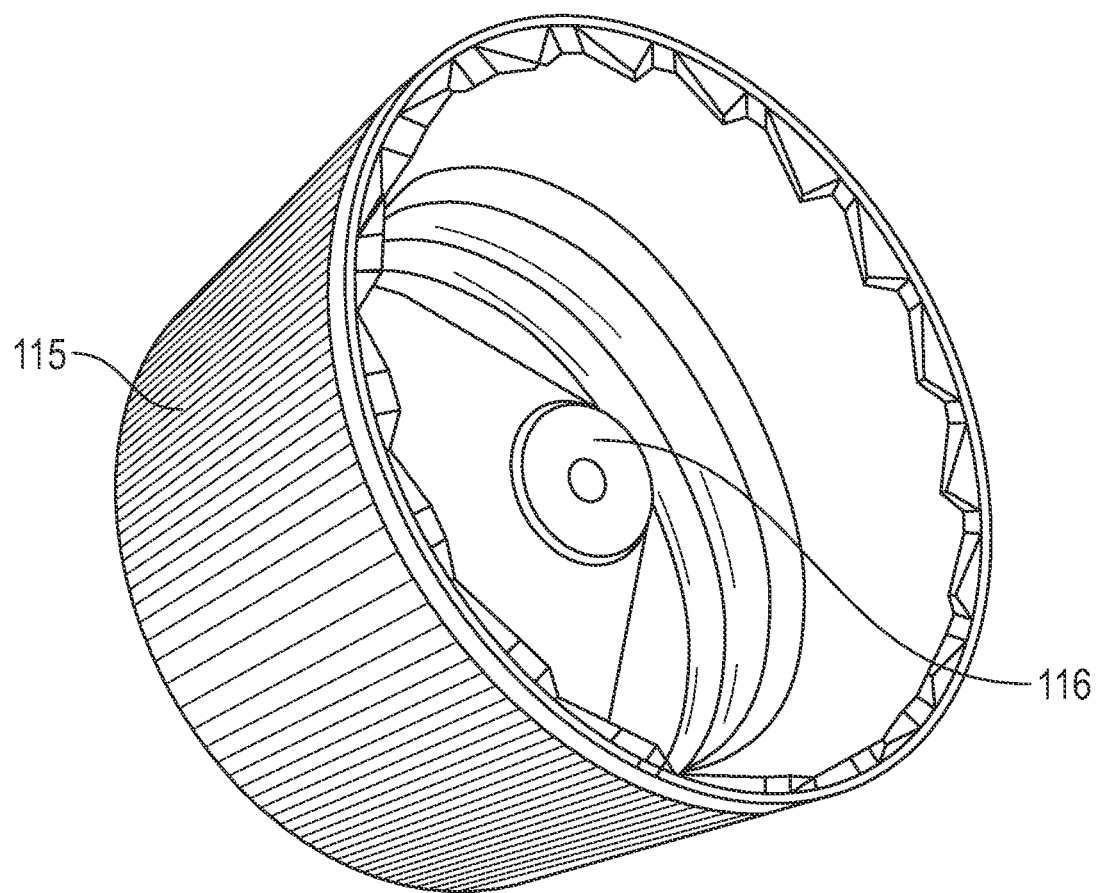
FIG. 4 is a view of a poly-cone insert inside the lid intended for the vial seen in FIGS. 1A-3.

The assembly [100] for transporting a corneal graft [105] that is prepared for endothelial keratoplasty. There exists a clear vial [110], also referred to as "the vial", which when assembled will contain 18-22 mL of cornea storage media [112], and a vial lid [115], preferably with a poly-seal cone insert (FIG. 4) on the interior side of the lid. The vial may have a base that is a rounded shape, a square shape, or the vial may be cylindrical with at least one flat plane positioned as a chord along the circumference of its surface.

The assembly [100] further includes a corneal tissue carrier, or graft carrier [120]. In certain embodiments, the corneal tissue carrier [120] may be a modified Jones tube, derivatives thereof, or another suitable tube-shaped tissue carrier. In one embodiment, the corneal tissue carrier [120] may be a modified Jones tube and will have rounded or oval openings measuring 2-4 mm in diameter, one of which is beveled, and 16-27 mm mm in length. In some embodiments, the corneal tissue carrier [120] may be formed from a polymer, a glass, or another suitable material. In specific embodiments, the corneal tissue carrier [120] may be formed from a biocompatible material (e.g., a biocompatible polymer, a biocompatible glass, etc.).

The corneal tissue which is a (corneal) graft or corneal tissue graft [105] is housed inside of an assembly [100] consisting of a transport assembly provided as a corneal tissue carrier [120], with beveled flexible tubing [125] attached to a larger, flanged end [126] of the corneal tissue carrier or (corneal) graft carrier or generic tissue carrier [120]. A locking connector which is a luer locking mechanism [130] consisting of both a barbed male end [132], and a female end luer locking connector [134] with an inlet luer locking mechanism [135], is removably coupled to a non-beveled flexible tubing [127], that is coupled to the top flange of a double-flanged spacer [128] measuring 10-21 mm in length, where the bottom flange of the double-flanged spacer [128] is removably coupled to the top opening of the beveled flexible tubing [125], which is removably coupled to the flanged end [126] of the graft carrier [120]. A luer locking cap [140] is designed to screw onto the female end luer locking connector [134] of the inlet luer locking mechanism [135]. A flexible cap [145], with holes arranged circumferentially (that may or may not be opposite each other) and perpendicular to the opening of the graft carrier [120], is removably coupled to the beveled end [150] of the graft carrier [120].

The caps [140, 145] may inhibit or restrict passage of a corneal tissue [105] out of the corneal tissue carrier [120]. In some embodiments, the caps [140,145] may allow or permit passage of fluid (e.g., a preservation fluid) into and/or out of the corneal tissue carrier [120]. In various embodiments, the caps [140, 145] may include one or more apertures (e.g., openings).

Any combination of caps or plugs (e.g., caps or plugs that allow passage of fluid and/or caps or plugs that inhibit passage of fluid) may be used with the corneal tissue carrier [120] disclosed herein.

The graft carrier [120] must be retrieved from the vial [110] in an upright position, making the vial [110] subject to tipping, spillage, and often susceptible to contamination of an otherwise sterile field. In order to provide needed additional external stability to prevent requiring assistance from an additional member of the surgical team to stabilize the vial, the vial [110] is supported with a removable non-sterile base [155]. The base [155] slides onto the vial [110] alleviating the need for additional assistance in removing the graft carrier [120] from the vial [110], and preventing the surgeon from having to touch the non-sterile external surface of the vial [110], or having a circulator hold the vial [110] to prevent tipping over at the time of retrieval. The base [155] can be injection molded, 3-D printed, or manufactured by any other such means that will produce the base as a single piece.

Figure 1B:
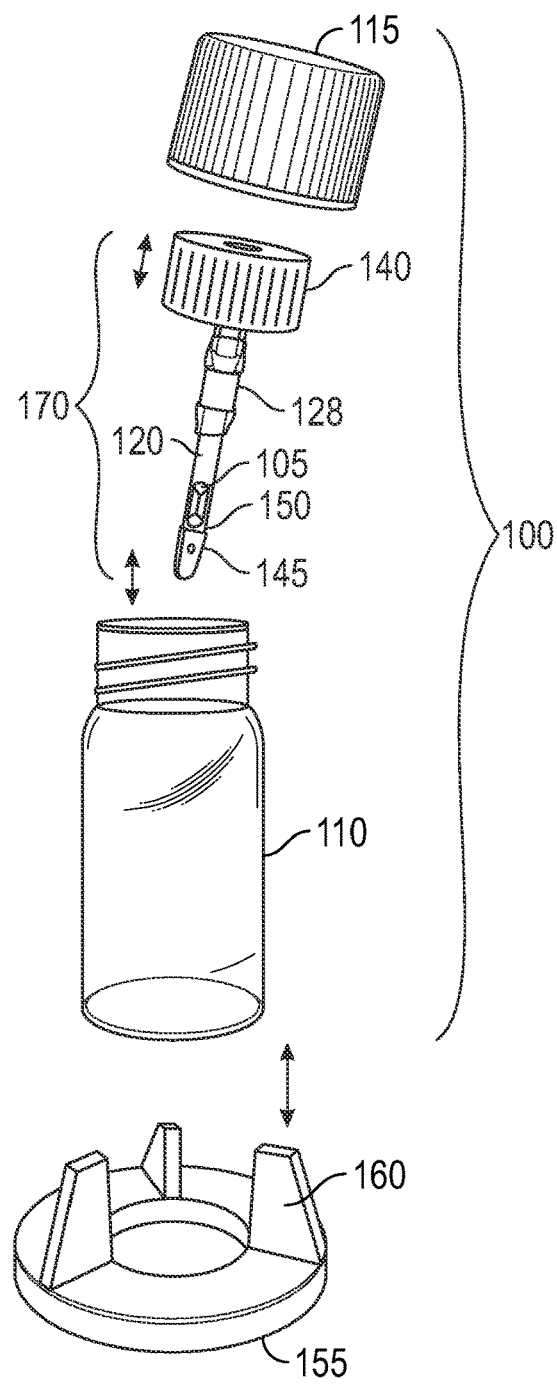
FIG. 1B is an exploded view of a corneal tissue sample assembly with assembled corneal tissue carrier and stabilization attachment.

FIG. 1B provides an exploded view of the assembly [100] with the corneal tissue carrier [120] in an assembled configuration (which is listed [170] and includes connected components of 140, 130, 127, 128, 125, 120, 105, and 145) for insertion into the vial [110]. The vial lid [115] secures the corneal tissue carrier [120] housing a corneal graft [105], complete with a luer locking cap [140] on one end and a flexible cap [145] on the opposite beveled end [150], within the vial [110]. The beveled end [150] of the corneal tissue carrier [120] is inserted into the vial [110], positioning the luer locking cap [140] at the opening of the vial [110].

The corneal tissue carrier [120] is not coupled to any portion of the vial [110] or vial lid [115], and is free within the vial [110], preferably maintained in place via light compression from the poly-seal cone insert (not shown) on the interior side of the vial lid [115] and the flexible cap [145] on the beveled end [150].

The vial [110] is placed within the prongs [160] of the base [155] in order to maintain an upright position and provide stability.

Figure 2:
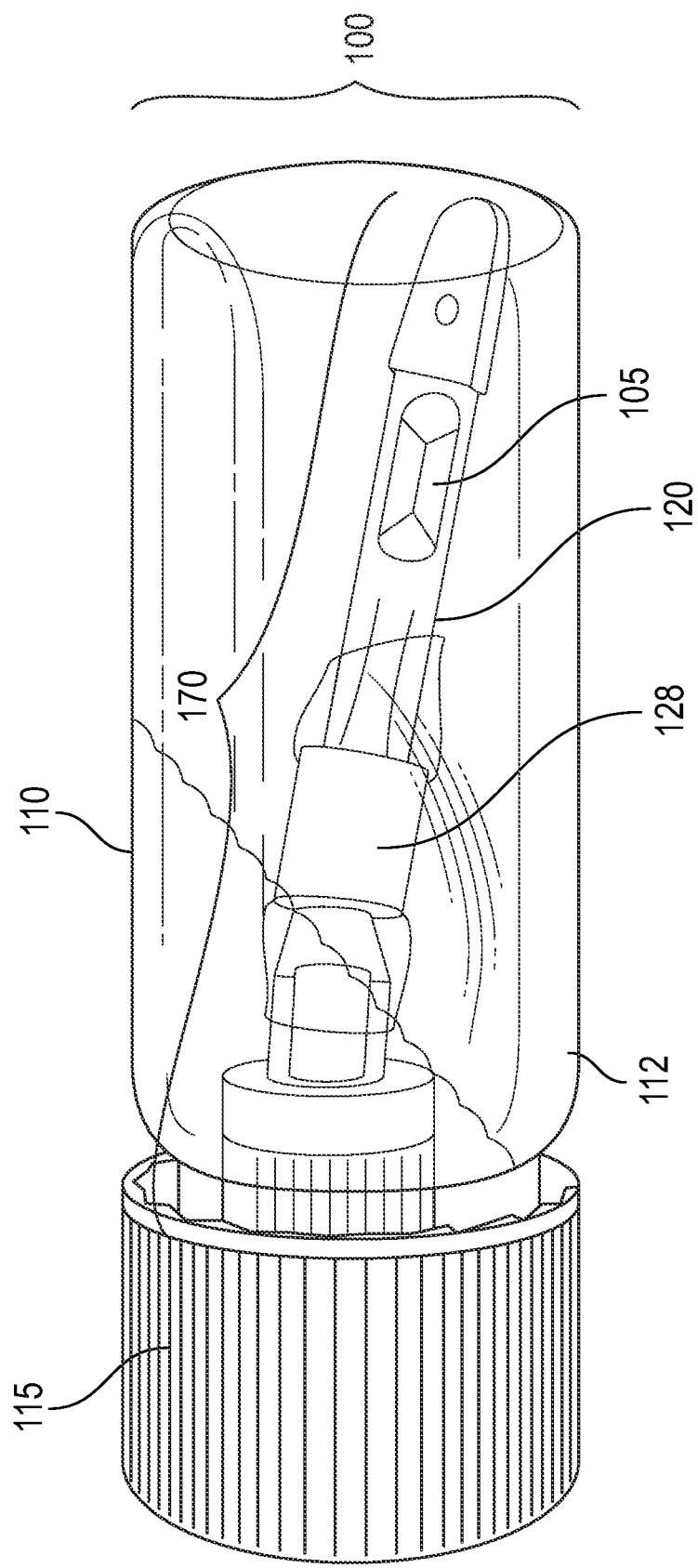
FIG. 2 is a perspective view of the corneal tissue sample assembly with corneal tissue carrier for supporting and transporting a graft.

FIG. 2 is a perspective view of an assembly, kit, or corneal tissue sample assembly [100] for storing, handling, transporting, viewing, evaluating, and/or shipping corneal tissue [105] in a closed, or assembled, configuration.

Transporting the corneal tissue carrier [120] with beveled flexible tubing [125] attached to the non-capped, flanged end [126] is shown in FIG. 2. The beveled flexible tubing [125] is 0.5-2.5 cm in length. A barbed male luer lock end having a diameter of 1/16-5/32 inches is inserted into the nonbeveled flexible tubing [127] that is connected to the top flange of the double-flanged spacer [128]. The opposite side of the barbed male connector is a female screw-on luer locking mechanism.

Neither the graft carrier [120] nor the double-flanged spacer [128] is designed to be connected directly to a syringe, and neither the outer edge of the graft carrier [120] nor the double-flanged spacer [128] can be inserted into the nozzle of a syringe, as the connection is secured through the use of an inlet luer-locking mechanism [135] which both prevents slippage of the graft carrier [120] and double-flanged spacer [128] from the syringe (not shown) and provides fluid communication with the graft carrier [120] and fluid control. The connection of the syringe to the locking connector [130] creates a pre-loaded syringe relieving the surgeon from having to load the graft [105] during the surgical procedure should he or she desire.

The syringe does not accompany the assembly [100] as a standard. Neither of the closure devices has been designed for connecting a collar or an adapter.

A collarless luer locking cap [140] is placed on the female end luer locking connector [134], the luer locking cap [140] possessing a small indention that will accept the tip of forceps, microforceps, hemostat, or other suitable sterile device, and allow for easy grasping of the assembly and retrieval from the vial [110]. When the graft [105] arrives to the surgeon, the surgeon must simply retrieve the completed assembly [170], remove the luer locking cap [140], and attach their own 3 or 5 mL syringe filled with balanced salt solution (BSS) to the female end luer locking connector [134]. Receiving a graft [105] that is pre-cut and pre-trephined to a pre-determined graft thickness saves up to 30 minutes of valuable surgeon operating room (OR) time while reducing risks associated with OR graft preparation and loading.

In order to be used for DSAEK corneal grafts in the specified vial [110] with poly-cone lid [115] and benefit from the same gentle compression forces during transit that are relieved when the lid [115] is removed, the corneal tissue carrier [120] beveled tubing [125], and double-flanged spacer [128] prior to inclusion of the nonbeveled tubing [127], luer locking mechanism [130] and collarless luer locking cap [140] must be 36-37 mm in length. The length includes a corneal tissue carrier [120] of 16-27 mm in length and a double-flanged glass tubing measuring 10-21 mm in length. In order for the corneal tissue graft [105] to be loaded into the tissue carrier [120], the graft [105] must be pulled into the corneal tissue carrier [120] using ophthalmic grasping forceps having a commercial availability of less than 37 mm grasping length. Current corneal tissue carriers having a length of 28 mm or more do not allow the ophthalmic grasping forceps to reach through the corneal tissue carrier [120] to grasp and pull the graft [105] into the carrier [120], without causing damage to the tissue/graft, and corneal tissue carriers [120] having a length of 37 mm or more may not be contained in a vial [110] with a poly-cone lid [115] without breakage of the carrier [120], the poly-cone insert [116], or the vial [110] itself.

By providing two separate glass sections, commercially available ophthalmic grasping forceps can be used to pull the DSAEK graft into a 16-27 mm long carrier section, that when attached to the 10-21 mm glass tubing section (and rest of the assembly), yields a completed assembly that is the correct length to fit in the vial/poly-cone lid setup and benefit from the same gentle compression our surgeons are familiar from the DMEK assembly/transport system of U.S. Pat. No. 10,806,558.

The DMEK assembly of U.S. Pat. No. 10,806,558 contains a single glass tube carrier measuring 37 mm in length and having a tapered graft carrier where the beveled end of the carrier has a much smaller opening than the non-capped flanged end of the graft carrier. The carrier is loaded via graft/fluid aspiration while the assembly is attached to a syringe. The corneal graft carrier accommodates a scrolled DMEK graft that is roughly 15-25 μm thick having a traditional scroll of cells on the outside.

The present disclosure provides a DSAEK assembly having 2-glass sections totaling 36-37 mm in length where the graft carrier [120] is a non-tapered straight glass tube having a much larger opening at the beveled end. The graft is mechanically pulled into the carrier using forceps. The corneal graft carrier [120] accommodates a tri-folded DSAEK graft having a thickness of less than roughly 80 μm, where the tri-fold positions the cells on the inside of the scroll. The thinner glass walls of the 16-27 mm beveled corneal graft carrier [120] maximizes the inner diameter of the tube, which minimizes the graft compression, in turn minimizing endothelial cell trauma.

FIG. 2 provides the assembly [100], complete with a corneal graft [105] within a corneal tissue carrier [120], in a closed configuration, where the corneal tissue carrier [120] and the vial [110] both contain sufficient cornea storage medium [112] to substantially immerse the graft [105] and the graft carrier [120], respectively. The cornea storage medium [112] can be disposed within at least a portion of the corneal tissue carrier [120] (e.g., when the corneal tissue carrier [120] is disposed within the vial [110]). In certain embodiments, the cornea storage medium [112] may be disposed only within at least a portion of the corneal tissue carrier [120]. In various embodiments, the cornea storage medium [112] may be disposed within the graft carrier [120] such that the corneal tissue [105] is substantially immersed in the cornea storage medium [112]. The closure is completed with the vial lid [115] compressively securing the completed assembly [170] within the vial [110], fast and simple retrieval from the vial [110] when the lid [115] is removed, easing the extraction for the surgeon, thus reducing retrieval time, potential for breakage of the corneal tissue carrier, and tipping of the assembly.

In certain embodiments, the cornea storage medium [112] may be OPTISOL™-GS, OPTISOL™, LIFE4° C.™ (NU-MEDIS™, Inc.), EUSOL-C™ (CORNEAL CHAMBER™, ALCHIMIA™, Sri), CORNEA COLD® (EUROBIO™), CORNISOL™ (AUROLAB™), a derivative thereof, or other suitable preservation fluid.

Figure 3:
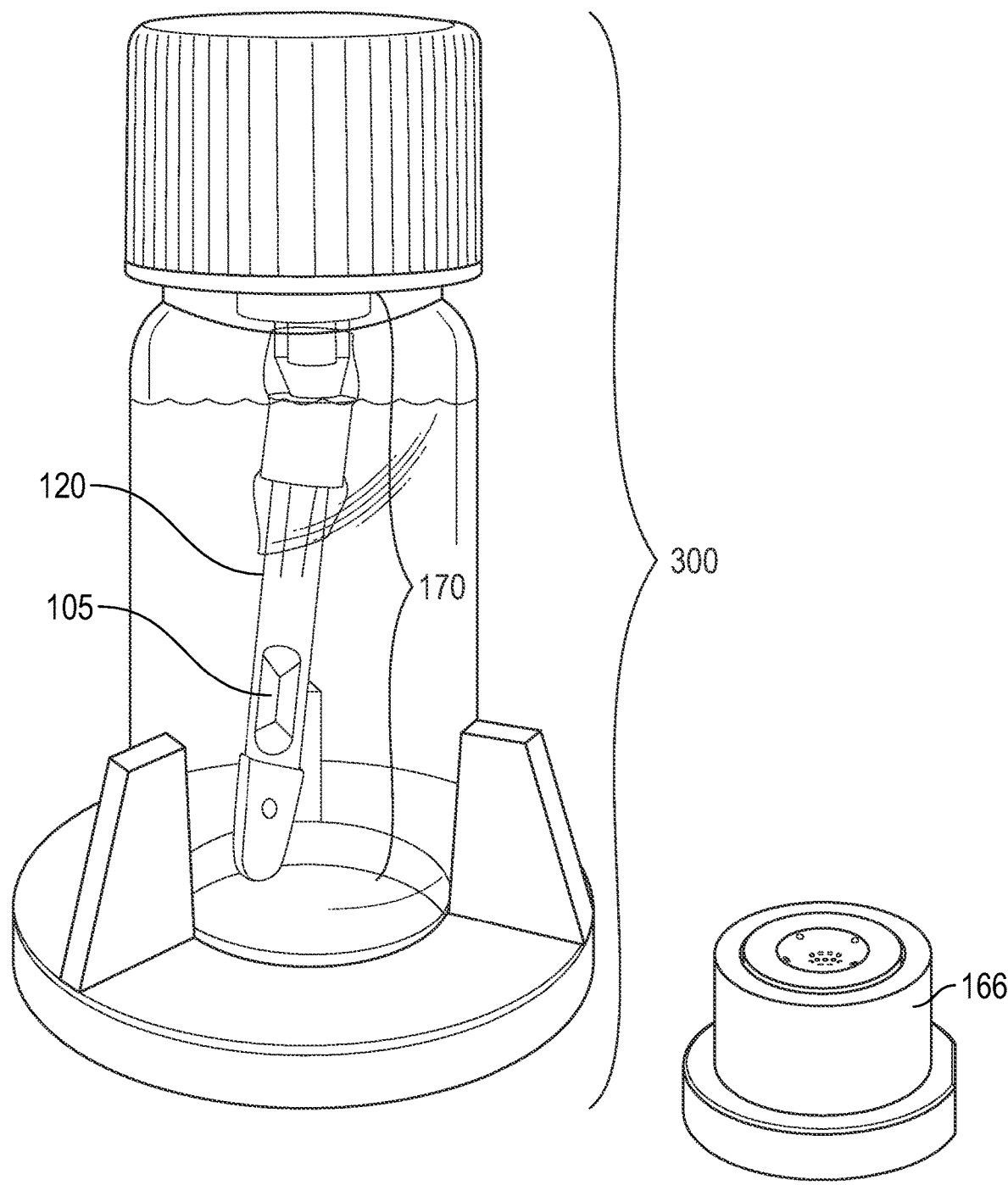
FIG. 3 is a side view of the corneal tissue sample assembly kit of FIGS. 1A-2.

FIG. 3 illustrates the assembly [100], in a closed configuration, removably coupled to the base [155] providing a kit [300] for storing, handling, transporting, viewing, evaluating, and/or shipping corneal tissue [105]. There are non-sterile components to the kit [300], including the base [155] that provides stability for the vial during the graft carrier's [120] retrieval from the vial [110]. Here a pedestal [166] that includes a top portion with an optional depository depression can be included with the kit [300] as, for example, the corneal tissue [105] may be rinsed and/or examined using the pedestal [166]. The pedestal (166) can be provided as another sterile addition to the kit [300]. The pedestal [166] can be injection molded, 3-D printed, or manufactured by any other such means that will produce the pedestal as a single piece.

It is important to understand and re-emphasize that items [145], [120], [125], [127], [128], [130], [140], and [155] can be/may be put together as a "sterile" kit [300] that other eye banks can use to prepare the assembly/devices described in conjunction with items [110] and [115]. This kit [300] allows for a graft to be securely loaded, supported, and/or securely transported as well as provide a secure and simple graft or implant as the graft or implant is introduced into a human or an animal body.

The corneal tissue sample could be a pre-stained, pre-cut and/or pre-defined corneal tissue graft, as no further removal from the corneal tissue carrier for manipulation or preparation should be required prior to the attachment of the luer-locking syringe, until administration of the graft to the patient, based on surgeon preference.

The assembly [100] can further include corneal tissue [105]. The corneal tissue [105] may be suitable for various forms of keratoplasty, lamellar keratoplasty, and/or endothelial keratoplasty (e.g., DMEK, PDEK, DSAEK, Ultra-thin DSAEK, Bowman's Membrane Transplantation, etc.). In some embodiments, the corneal tissue [105] may be a graft comprising corneal endothelium and Descemet's membrane. In some other embodiments, the corneal tissue [105] may include corneal endothelium, Descemet's membrane, and/or pre-Descemet's membrane. In particular embodiments, the corneal tissue [105] may be a DSAEK or UT-DSAEK graft or a graft suitable for a DSAEK or UT-DSAEK procedure. In alternative embodiments, the corneal tissue [105] may also include stroma. The cellular structures comprising the corneal tissue [105] may be primary cells from a single donor or cultured via ex vivo cellular expansion methodology. As shown, the corneal tissue [105] may be disposed within the corneal tissue carrier [120].

In some embodiments, at least a portion of each of the vial [110] and the corneal tissue carrier [120] may be substantially transparent, with the preferred transparency being clear, such that the corneal tissue [105] can be visible to a user. For example, the corneal tissue [105] may be disposed within the corneal tissue carrier [120], and the corneal tissue carrier [120] including the corneal tissue [105] may be further disposed within the vial [110]. In such configurations, the substantial transparency of the vial [110] and the corneal tissue carrier [120] may allow or permit the user to visualize the corneal tissue [105]. In certain embodiments, the corneal tissue carrier [120] and the vial [110] are substantially transparent and/or substantially clear such that a user may visualize and/or evaluate the corneal tissue [105] disposed within the corneal tissue carrier [120] and the vial [110] using corneal tissue evaluation instruments and/or methods such as specular microscopy, slit-lamp biomicroscopy, light microscopy, and/or optical coherence tomography.

In some embodiments, the corneal tissue carrier [120] is configured to be coupled to a syringe via a luer-locking mechanism, for example, the flanged end [126] of the corneal tissue carrier [120] is coupleable to a luer locking connector designed to accept the tip of a syringe (not shown). In certain embodiments, a portion of medical tubing may be coupled to the corneal tissue carrier [120]. In certain embodiments, the medical tubing may be integral with the corneal tissue carrier [120]. In certain other embodiments, each of the medical tubing and the corneal tissue carrier [120] may be discrete components.

A cornea storage fluid [112], or preservation fluid, can be disposed within at least a portion of the inner portion of the vial [110]. Additionally, the preservation fluid [112] can be disposed within at least a portion of the inner cavity of the corneal tissue carrier [120] such that the corneal tissue [105] is substantially immersed in the cornea storage fluid [112].

As described above, the corneal tissue sample may be a graft comprising corneal endothelium and Descemet's membrane. The corneal tissue sample may be suitable for various forms of lamellar keratoplasty (e.g., DMEK, PDEK, DSAEK, Ultra-thin DSAEK, etc.). In some embodiments, the corneal tissue sample may be a graft comprising corneal endothelium and Descemet's membrane. In some other embodiments, the corneal tissue [105] may include corneal endothelium, Descemet's membrane, and/or pre-Descemet's membrane. In particular embodiments, the corneal tissue sample is a DSAEK or UT-DSAEK graft or a graft suitable for a DSAEK or UT-DSAEK procedure. In specific embodiments, the corneal tissue sample may also include stroma. The cellular structures comprising the corneal tissue [105] may be primary cells from a single donor or cultured via ex vivo cellular expansion methodology.

The method of processing the corneal tissue sample may also include coupling a cap to an opening of the corneal tissue carrier. As discussed above, the cap may limit or inhibit passage of the corneal tissue sample out of the corneal tissue carrier. Furthermore, the cap may allow or permit passage of the preservation fluid into and out of the corneal tissue carrier.

In some embodiments, a method of administering a corneal tissue sample may include obtaining a corneal tissue sample assembly. The assembly, as described above, may include a corneal tissue carrier and a corneal tissue sample disposed within the corneal tissue carrier. A method of administering a corneal tissue sample may further include administering or transplanting the corneal tissue sample to a subject. In some embodiments, the subject may be a patient in need of a corneal tissue transplant.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

References to approximations are made throughout this specification, such as by use of the term "substantially." For each such reference, it is to be understood that, in some embodiments, the value, feature, or characteristic may be specified without approximation. For example, where qualifiers such as "about" and "substantially" are used, these terms include within their scope the qualified words in the absence of their qualifiers. For example, where the term "substantially transparent" is recited with respect to a feature, it is understood that in further embodiments, the feature can have a precisely transparent configuration.

Numerous references have been made to printed publications throughout this specification. Each of the above-cited references and printed publications is individually incorporated herein by reference in its entirety.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description.

Without further elaboration, it is believed that one skilled in the art can use the preceding description to utilize the invention to its fullest extent. The claims and embodiments disclosed herein are to be construed as merely illustrative and exemplary, and not a limitation of the scope of the present disclosure in any way. It will be apparent to those having ordinary skill in the art, with the aid of the present disclosure, that changes may be made to the details of the above-described embodiments without departing from the underlying principles of the disclosure herein. In other words, various modifications and improvements of the embodiments specifically disclosed in the description above are within the scope of the appended claims. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified. The scope of the invention is therefore defined by the following claims and their equivalents.

I claim:

1. A kit comprising components that together complete a Descemet's Stripping Automated Endothelial Keratoplasty (DSAEK) fitted assembly that provides a corneal graft carrier for supporting and transporting a graft or implant that is a tissue wherein said kit comprises; both beveled and non-beveled tubing, a vial with a vial lid that includes a poly-cone insert so that said vial lid and a vented cap on said DSAEK fitted assembly compressively secures said DSAEK fitted assembly corneal graft carrier within said vial, a support base that provides support so that said vial is able to stand upright and remain motionless, a collarless luer locking cap, a luer locking connector that includes both a female luer locking end and a barbed male end, wherein said female luer locking end connects with said luer locking cap and wherein said barbed male end is slideably coupled to flexible, nonbeveled tubing, that completes a connection between additional beveled tubing and two glass sections such that one glass section is a corneal tissue graft carrier holding portion that is a non-tapered straight glass tube with a largest opening at a beveled end of said straight glass tube and a second glass section with a spacer portion that provides a rigid connection between beveled flexible tubing and nonbeveled flexible tubing so that a double-flanged glass tube connects to said straight glass tube and luer lock connector and such that said DSAEK assembly provides said graft or implant that is a tissue contained within said complete DSAEK fitted assembly.

2. The kit of claim 1, wherein beveled flexible tubing is connected to a bottom flange of a double-flanged glass tubing and is further connected to a nonbeveled flexible tubing and luer locking mechanism wherein an inlet luer locking mechanism and complete fitted assembly reduces surgical operating room (OR) time by at least two minutes and wherein said graft is tissue.

3. The kit of claim 1, wherein said corneal graft carrier provides a lack of counter-resistive forces so that retrieval of said graft or implant that is tissue from said vial is extracted by one or more medical professionals, thus reducing retrieval time, potential for breakage of said corneal graft carrier, and reduces and/or eliminates risk of tipping said completed assembly.

4. The kit of claim 1, wherein a folded DSAEK graft is accommodated that is in a thickness range of less than 80 μm thick and wherein said folded DSAEK graft includes a traditional layer of endothelial cells on an inside portion of said DSAEK graft.

5. The kit of claim 1, wherein said female luer locking end connects to a syringe after said collarless luer locking cap has been removed, from said female luer locking end so that said completed fitted assembly provides an ability to directly eject tissue into a patient's eye, specifically an anterior chamber and/or cornea by a surgeon, and wherein said tissue is held within said corneal graft carrier with a flexible cap with orifices arranged circumferentially and perpendicular to an opening of said corneal graft carrier that is removably coupled with a beveled end of said corneal graft carrier.

6. The kit of claim 1, wherein said corneal graft carrier is a corneal tissue carrier that carries corneal tissue and wherein said corneal graft carrier is a modified ophthalmic tube that includes a modified Jones tube or other modified tube-shaped device.

7. The kit of claim 6, wherein said collarless luer locking cap includes a small indention that accepts a tip of at least one of a group consisting of forceps, microforceps, hemostat, and suitable sterile device that allows for ease of grasp of said tissue from said completed fitted assembly and ease of retrieval of tissue from said vial and wherein said vial has a base that is either a circular or square-shaped base.

8. The kit of claim 7, wherein said corneal graft carrier is comprised of either transparent or translucent glass, thermoplastics, and/or silicone polymers, and is designed to hold a lamellar cornea graft, that is a scrolled or folded corneal tissue graft, from either a primary cell donor or obtained via ex vivo cellular expansion methods that can be seen and inspected by a surgeon prior to and during an operation that utilizes said corneal tissue.

9. The kit of claim 1, wherein said beveled and non-beveled tubing is flexible and pliable tubing and wherein said tubing comprises materials that are flexible, pliable or rigid materials selected from one or more of a group consisting of silicone, silicone rubber, thermoplastics, thermosets, metals, and ceramics.

10. The kit of claim 1, wherein a syringe is included with said kit.

11. A Descemet's Stripping Automated Endothelial Keratoplasty (DSAEK) fitted assembly that is a corneal graft carrier for supporting and transporting a graft or implant that is a tissue wherein said fitted assembly further comprises both beveled and non-beveled tubing, a vial with a vial lid that includes a poly-cone insert so that said vial lid and a vented cap on said DSAEK fitted assembly compressively secures said DSAEK fitted assembly corneal graft carrier within said vial, a support base that provides support so that said vial is able to stand upright and remain motionless, a collarless luer locking cap, a luer locking connector that includes both a female luer locking end and a barbed male end, wherein said female luer locking end connects with said luer locking cap and wherein said barbed male end is slideably coupled to flexible, nonbeveled tubing, that completes a connection between additional beveled tubing and two glass sections such that one glass section is a corneal graft carrier with a corneal tissue graft carrier holding portion that is a non-tapered straight glass tube with a largest opening at a beveled end of said straight glass tube and a second glass section with a spacer portion that provides a rigid connection between beveled flexible tubing and non-beveled flexible tubing so that a double-flanged glass tube connects to said straight glass tube and luer lock connector and such that said DSAEK assembly provides said graft or implant that is a tissue contained within said complete DSAEK fitted assembly.

12. The fitted assembly of claim 11, wherein beveled flexible tubing is connected to a bottom flange of a double-flanged glass tubing and is further connected to a nonbeveled flexible tubing and luer locking mechanism wherein an inlet luer locking mechanism and complete fitted assembly reduces surgical operating room (OR) time by at least two minutes and wherein said graft is tissue.

13. The fitted assembly of claim 11, wherein said corneal graft carrier provides a lack of counter-resistive forces so that retrieval of said graft from said vial is extracted by one or more medical professionals, thus reducing retrieval time, potential for breakage of said corneal graft carrier, and reduces and/or eliminates risk of tipping said completed assembly.

14. The assembly of claim 11, wherein a folded DSAEK graft is accommodated that is in a thickness range of less than 80 µm thick and wherein said folded DSAEK graft includes a traditional layer of endothelial cells on an inside portion of said folded DSAEK graft.

15. The assembly of claim 11, wherein said female luer locking end connects to a syringe after said collarless luer locking cap has been removed from said female luer locking end so that said DSAEK completed fitted assembly provides an ability to directly eject tissue by a surgeon, and wherein said tissue is held within said tissue carrier.

16. The assembly of claim 11, wherein said corneal graft carrier is a corneal tissue carrier that carries corneal tissue and wherein said corneal tissue carrier is a modified Jones tube or a modified tube-shaped device.

17. The assembly of claim 16, wherein said collarless luer locking cap includes a small indention that accepts a tip of at least one of a group consisting of: forceps, microforceps, hemostat, and suitable sterile device that allows for ease of grasp of said tissue from said completed fitted assembly and ease of retrieval of said tissue from said vial and wherein said vial has a base that is either a circular or square-shaped base.

18. The assembly of claim 16, wherein said corneal tissue carrier is comprised of either transparent or translucent glass, thermoplastics, and/or silicone polymers, and is designed to hold a lamellar cornea graft, that includes a scrolled or folded corneal tissue graft, from either a primary cell donor or obtained via ex vivo cellular expansion that can be observed and inspected by a surgeon prior to and during an operation that utilizes corneal tissue.

19. The assembly of claim 18, wherein said beveled and non-beveled tubing is flexible and pliable tubing and wherein said tubing comprises materials selected from one or more of a group consisting of silicone, silicone rubber, thermoplastics, thermosets, metals, and ceramics.

20. A method for performing tissue repair or replacement surgery via a two-step process that includes utilizing a Descemet's Stripping Automated Endothelial Keratoplasty (DSAEK) fitted assembly within a vial filled with storage media fluid and a graft or implant for supporting and transporting said graft or implant that is a tissue such that when said graft or implant held within said assembly arrives for surgery, a surgeon that acts alone inspects said graft or implant and said surgeon retrieves said fitted assembly that functions as a graft or implant carrier, removes a luer locking cap and attaches a syringe filled with a balanced salt solution (BSS) to a female luer locking connector wherein said fitted assembly includes flexible tubing and an inlet luer-locking mechanism that provides a lack of counter resistant force allowing said surgeon access to said graft or implant and completion of surgery to replace or repair corneal tissue.

21. The method of claim 20, wherein tissue repair or replacement surgery is a lamellar keratoplasty surgery utilizing primary cells from a donor, or cells that are obtained via ex vivo methods, and includes endothelial keratoplasty, specifically, Descemet's Stripping Automated Endothelial Keratoplasty (DSAEK) or Ultrathin DSAEK (UT-DSAEK) surgery.

22. A method of using a completed Descemet's Stripping Automated Endothelial Keratoplasty (DSAEK) fitted assembly for supporting and transporting a graft that is a tissue or implant that is a tissue, wherein said DSAEK fitted assembly comprises; a vial with a vial lid that includes a poly-cone insert so that said vial lid and a vented cap on said DSAEK fitted assembly compressively secures said DSAEK fitted assembly that includes a graft carrier within said vial, a support base that provides support so that said vial is able to stand upright and remain motionless, a collarless luer locking cap, a luer locking connector that includes both a female luer locking end and a barbed male end, wherein said female luer locking end connects with said luer locking cap and wherein said barbed male end is slideably coupled to flexible, nonbeveled tubing, that completes a connection between additional beveled tubing and two glass sections such that one glass section is a corneal tissue graft carrier holding portion that is a non-tapered straight glass tube with a largest opening at a beveled end of said straight glass tube and a second glass section with a spacer portion that provides a rigid connection between beveled flexible tubing and nonbeveled flexible tubing so that a double-flanged glass tube connects to said straight glass tube and luer lock connector and such that said DSAEK fitted assembly provides a graft contained within said complete DSAEK fitted assembly.

23. The method of claim 22, wherein a tissue carrier is a corneal tissue carrier that carries corneal tissue and wherein a corneal tissue carrier is a modified Jones tube or other a modified tube-shaped device and said corneal tissue carrier includes a flexible cap with orifices arranged circumferentially and perpendicular to an opening of said corneal tissue carrier that is removably coupled with a beveled end of said tissue carrier.

24. The method of claim 22, wherein said collarless luer locking cap includes a small indention that accepts a tip of at least one of a group consisting of: forceps, microforceps, hemostat, and suitable sterile device that allows for ease of grasp of said corneal tissue carrier from said completed fitted assembly and ease of retrieval of corneal tissue from said vial.

25. The method of claim 22, wherein said corneal tissue carrier is comprised of either transparent or translucent glass, thermoplastics, and/or silicone polymers, and is designed to hold a lamellar cornea graft, that includes a scrolled corneal tissue graft, from either a primary cell donor or obtained via ex vivo cellular expansion that is observed and inspected by a surgeon prior to and during an operation that utilizes said corneal tissue.

26. The method of claim 22, wherein tubing is flexible and pliable tubing and wherein said tubing comprises materials selected from one or more of a group consisting of silicone, silicone rubber, thermoplastics, thermosets, metals, and ceramics.

* * * * *